(12) United States Patent
Hogan

(10) Patent No.: US 6,943,254 B2
(45) Date of Patent: Sep. 13, 2005

(54) SYNTHESIS OF PYRAZINYL PYRIDINE-3-SULFONAMIDE COMPOUNDS

(75) Inventor: Philip John Hogan, Macclesfield (GB)

(73) Assignee: Astrazeneca UK Limited, London (GB)

( * ) Notice: Subject to any disclaimer, the term of this patent is extended or adjusted under 35 U.S.C. 154(b) by 86 days.

(21) Appl. No.: 10/348,229

(22) Filed: Jan. 22, 2003

(65) Prior Publication Data

US 2003/0162973 A1 Aug. 28, 2003

Related U.S. Application Data

(62) Division of application No. 09/380,478, filed as application No. PCT/GB98/00651 on Mar. 3, 1998, now Pat. No. 6,531,605.

(30) Foreign Application Priority Data

Mar. 7, 1997 (GB) .............................. 9704762

(51) Int. Cl.⁷ .......................................... C07D 241/22
(52) U.S. Cl. ........................................................ 544/405
(58) Field of Search ........................................ 544/405

(56) References Cited

U.S. PATENT DOCUMENTS

| | | | |
|---|---|---|---|
| 3,947,512 A | 3/1976 | Gengnagel et al. | 260/543 |
| 4,714,700 A | 12/1987 | Fournier et al. | |
| 6,258,817 B1 * | 7/2001 | Bradbury et al. | 514/255.05 |

FOREIGN PATENT DOCUMENTS

| | | |
|---|---|---|
| DE | 859461 | 12/1952 |
| WO | 9640681 | 12/1996 |

OTHER PUBLICATIONS

Rondestvedt, C.S. Jr., Organic Reactions, vol. 24, 1976, John–Wiley, New York, pp. 238.*
Gilbert, Everett E., "Recent Developments in Preparative Sulfonation and Sulfation," Synthesis, 1969, No. 1, pp. 3–10.
Prinsen, A.J. et al., "The Synthesis of Arylsulfonyl Halides," Rec. Trav. Chem., 1965, pp. 24–29, vol. 84.
Saunders, K.H. et al., Aromatic Diazo Compounds (Third Ed.), Section 15.24, pp. 727–730.
Hodson, D., et al., "Product Determination by a Catalyst," School Sci. Rev., 1973, pp. 768–769, 1973.
Wirth, D.D., Synthetic Reagents, 1995, pp. 4873–4876.

Deeb, A., et al., *Monatshefte für Chemie*, 1990, pp. 281–287, 121(4). Springer–Verlag.
Rondestvedt, C.S., Jr., "Chapter 3 Arylation of Unsaturated Compounds by Diazonium Salts (The Meerwein Arylation Reaction)," *Organic Reactions*, vol. 24, 197, John–Wiley, New York, pp. 226–259.

\* cited by examiner

Primary Examiner—Thomas C. McKenzie
(74) Attorney, Agent, or Firm—Rothwell, Figg, Ernst & Manbeck

(57) ABSTRACT

A process for the manufacture of:

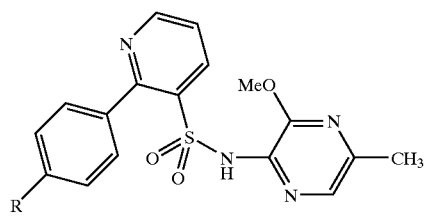

I wherein R is (1–4C)alkyl, carboxyl(1–4C)alkyl or 1,3,4-oxadiazol-2-yl comprises:
(a) reaction of the diazonium salt of 3-amino-2-chloropyridine with thionyl chloride in water and an electron transfer catalyst;
(b) reaction with isobutyl-(3-methoxy-5-methylpyrazin-2-yl)carbamate and an alkali metal hydride in inert solvent; and
(I) where R is (1–4C)alkyl, carboxy(1–4C)alkyl:
(c) reaction with a boronic acid:

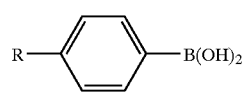

II (or an anhydride or ester therof) in the presence of a base and a palladium or nickel catalyst in solvent; and removal of the isobutoxy carbonyl group; or
(ii) where R is 1,3,4-oxadiazol-2-yl
(c) reaction with 4-methoxycarbonylphenylboronic acid (or an anhydride or ester thereof) with a source fluoride ion under aqueous conditions;
(d) removal of the isobutoxycarbonyl protecting group;
(e) conversion of the methyl ester group to the hydrazide; and
(f) conversion to a 1,3,4-oxadiazol-2-yl moiety.

2 Claims, No Drawings

SYNTHESIS OF PYRAZINYL PYRIDINE-3-SULFONAMIDE COMPOUNDS

This application is a divisional of U.S. patent application Ser. No. 09/380,478, filed Oct. 25, 1999, now U.S. Pat. No. 6,531,605, which was a 371 filing of PCT Application No. PCT/GB98/00651, filed Mar. 3, 1998 which claims priority from GB Application 9704762, filed Mar. 7, 1997.

This invention concerns a novel chemical process and, more particularly, it concerns a novel chemical process for the manufacture of pyridinesulfonyl chlorides and certain benzenesulfonyl chlorides.

Pyridinesulfonyl chlorides and benzenesulfonyl chlorides are useful in the manufacture of compounds having a variety of uses, such as in the manufacture of pharmaceuticals or herbicides. For example 2-chloropyridine-3-sulfonyl chloride is particularly useful in the production of the endothelin antagonists described in International Patent Application, Publication No. WO 96/40681.

A number of methods are known for preparing pyridinesulfonyl chlorides (such as 2-chloropyridine-3-sulfonyl chloride) and benzenesulfonyl chlorides. One such method involves reaction of the diazonium salt of the corresponding aminopyridine (such as 3-amino-2-chloropyridine) or aromatic amine with sulfur dioxide in the presence of acetic acid and using CuCl or $CuCl_2$ as catalyst, followed by isolation of the product by solvent extraction. Such a method is disclosed in WO 96/40681 and European Patent-Application, Publication Nos. 733629 and 618209. Similar methods are disclosed in *Synthesis*, (1969), 6, No. 1, pages 3–10 and *Rec. Trav. Chim.*, (1965), 84, pages 24–29, A disadvantage with carrying out this process on a large scale is the difficulty associated with the isolation of the product free of impurities at the end of the reaction. In particular it is often difficult on a large scale to obtain the product free of acetic acid or prevent hydrolysis of the product to the corresponding sulfonic acid on work-up. A further disadvantage of carrying out this process on a large scale is the use of the gaseous reagent, sulfur dioxide. These disadvantages make this process unattractive for operation on a commercial scale.

Surprisingly, a process has now been discovered for the manufacture of pyridine sulfonyl chlorides and certain benzenesulfonyl chlorides which avoids the use of both acetic acid and sulfur dioxide gas and which overcomes the isolation problems encountered with the known process.

According to the invention there is provided a process for the manufacture of a pyridinesulfonyl chloride or a benzenesulfonyl chloride in which the benzene ring bears one or more electron-withdrawing groups which comprises reaction of the diazonium salt of an aminopyridine or aminobenzene in which the benzene ring bears one or more electron-withdrawing groups with a mixture of thionyl chloride in water, in the presence of an electron transfer catalyst.

A particular aspect of the present invention is a process for the manufacture of a pyridinesulfonyl chloride which comprises reaction of the diazonium salt of an aminopyridine with a mixture of thionyl chloride in water, in the presence of an electron transfer catalyst.

A further particular aspect of the present invention is a process for the manufacture of a benzenesulfonyl chloride in which the benzene ring bears one or more electron-withdrawing groups (more particularly one or two electron-withdrawing groups) which comprises reaction of the diazonium salt of an aminobenzene, in which the benzene ring bears one or more electron-withdrawing groups, with a mixture of thionyl chloride in water, in the presence of an electron transfer catalyst.

It will be appreciated that, where a pyridinesulfonyl chloride or an aminopyridine is referred to, the pyridine ring may be unsubstituted or may bear one or more substituents. A particular substituent includes, for example, an electron-withdrawing substituent.

A preferred electron transfer catalyst includes, for example, cupric chloride ($CuCl_2$) and cuprous chloride (CuCl), especially the latter. Preferably 0.012 to 0.05 equivalents of catalyst (per equivalent of amino compound) are used.

It is well known that functional groups or substituents can be classified as electron-withdrawing (–I) or electron-donating (+I) groups relative to hydrogen, as disclosed by J. March in Advanced Organic Chemistry, Fourth Edition, Wiley & Sons. Typical electron-withdrawing groups are referred to or listed in the above publication and these are included herein by reference. Particular electron-withdrawing groups include, for example, chloro, bromo, cyano, nitro and carboxy.

The preparation of the diazonium salt of a primary aromatic or heteroaromatic amine is well known in the art of organic chemistry, by reaction of the amine with nitrous acid. For the process of the present invention it is convenient to generate the nitrous acid in situ by the conventional method of reacting an alkali metal nitrite, especially sodium nitrite, with a mineral acid, especially hydrochloric acid, in the presence of the amino compound. The diazotisation reaction is generally carried out at a temperature in the range of about +5 to –10° C., and preferably at about +1 to –4° C. It is preferred to use about 1 to 1.2 equivalents of alkali metal nitrite and 3 to 20 (more preferably 11 to 13) equivalents of concentrated (approximately 36%) hydrochloric acid (per equivalent of amino compound). When the starting material is an aminobenzene bearing one or more electron-withdrawing groups, it is preferred that the amine is added to the mineral acid and this mixture heated at 30 to 50° C. for 10 to 60 minutes (to ensure complete salt formation) prior to cooling and addition of the aqueous sodium nitrite solution. The water charge to dissolve the sodium nitrite is generally between 1 to 5 volumes based on the input weight of amino compound, although solid nitrite may alternatively be added portionwise to the mixture of the amine in hydrochloric acid. It is preferable to use the diazonium salt solution or slurry so generated immediately after preparation because of the instability of the diazoniun salt, maintaining the temperature of the solution or slurry at about +1 to –4° C. during the addition.

It is preferred that 2 to 12 equivalents of thionyl chloride are used per equivalent of amino compound, and especially 4 to 5 equivalents.

It is preferred that the water charge for thionyl chloride dissolution is between 5 to 30 volumes (and more preferably 10 to 20 volumes) of water, based on the input weight of amino compound.

It is preferred that the thionyl chloride and water mixture is maintained at 18–25° C., and conveniently at about ambient temperature, for 1 to 48 hours, and conveniently 15 to 20 hours (for example overnight), prior to reaction with the diazonium salt.

It is preferred that the solution of the diazonium salt is added over as short a time as possible consistent with maintaining the exothermic reaction at a temperature between –10 and +5° C., and preferably between –4 and +1° C. After addition it is preferred that the reaction is maintained at about this temperature for 15 to 90 minutes.

The product may be isolated by extraction into a suitable solvent, such as a hydrocarbon, chlorinated hydrocarbon or ether solvent immiscible with water, such as dichloromethane, diethyl ether or preferably toluene. The absence of acetic acid in the reaction mixture means that difficulties associated with the presence of acetic acid in the solvent extract (and its subsequent removal) are avoided. The advantage of using toluene as the extraction solvent is that the extract can be washed with water and any residual traces of water and entrained HCl removed by azeotropic distillation to give the product as a solution in toluene, which can then be used directly in a subsequent reaction or the toluene can be removed under vacuum to give the product which may be recrystallised in high purity, for example from a non-polar solvent such as n-hexane, isohexane or cyclohexane.

Alternatively, where the product is a solid sulfonyl chloride, it may precipitate from the reaction mixture and be collected by filtration instead of by solvent extraction.

The process of the invention is particularly suitable for preparing 2-halogenopyridine-3-sulfonyl chlorides such as 2-chloropyridine-3-sulfonyl chloride.

A further surprising advantage found with the process of the present invention when it is used to prepare 2-chloro-3-pyridinesulfonyl chloride is that the product precipitates from the reaction mixture in high purity as the free base and can be collected by filtration. It is believed that all previously known methods for preparing 2-chloro-3-pyridinesulfonyl chloride from the diazonium salt of 3-amino-2-chloropyridine require isolation by extraction, because of the use of acetic acid in the reaction.

The present invention also provides a process for preparing certain endothelin antagonists disclosed in WO 96/40681, which is incorporated herein by reference.

Thus, according to another aspect, the invention provides a process for the preparation of a compound of the formula I

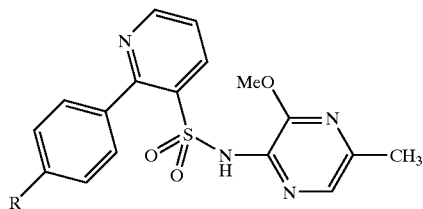

I or a pharmaceutically acceptable salt thereof, wherein R is (1–4C)alkyl or carboxy(1–4C)alkyl which comprises the steps of:

(a) reaction of the diazonium salt of 3-amino-2-chloropyridine with a mixture of thionyl chloride in water, in the presence of an electron transfer catalyst, to give 2-chloropyridine-3-sulfonyl chloride;

(b) reaction of 2-chloropyridine-3-sulfonyl chloride with isobutyl N-(3-methoxy-5-methylpyrazin-2-yl)carbamate in the presence of an alkali metal hydride in an inert solvent to give 2-chloro-N-isobutoxycarbonyl-N-(3-methoxy-5-methylpyrazin-2-yl)pyridine-3-sulfonamide;

(c) reaction of 2-chloro-N-isobutoxycarbonyl-N-(3-methoxy-5-methylpyrazin-2-yl)pyridine-3-sulfonamide with a boronic acid of the formula II,

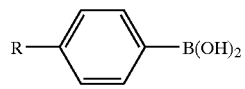

II (or an anhydride or ester thereof) in the presence of a base and in the presence of a palladium (0), palladium (II), nickel (0) or nickel (II) catalyst in a suitable solvent; followed by removal of the isobutoxycarbonyl protecting group;

whereafter, when a pharmaceutically acceptable salt of a compound of formula I is required, it is obtained by reaction with the appropriate acid or base affording a physiologically-acceptable ion, or by any other conventional salt formation procedure.

Step (a) may be carried out as described above.

Step (b) may be carried out, for example, using an alkali metal hydride (such as sodium or potassium hydride) in a inert solvent such as DMF, pyridine or toluene. The reaction is carried out at a temperature in the range of, for example, 0° C. to 70° C. A typical example of step (b) is described in Example 1 (ii) of WO 96/40681. The compound isobutyl N-(3-methoxy-5-methylpyrazin-2-yl)carbamate may, for example, be obtained as described in Example 1 of WO 96/40681

In Step (c), suitable catalysts include, for example, tetrakis(triphenylphosphine)nickel(0), bis(triphenylphosphine)nickel(II)chloride, nickel(II)chloride, bis(triphenylphosphine)palladium(II)chloride, palladium(II) chloride and tetrakis(triphenylphosphine)palladium(0), of which the latter is a preferred catalyst. A suitable base for use in the reaction is, for example, an alkali metal alkoxide (such as sodium methoxide or sodium ethoxide), an alkali metal hydroxide (such as sodium or potassium hydroxide), an alkali metal carbonate (such as sodium or potassium carbonate), or an organic base (such as tri(1–6C)alkylamine, for example, triethylamine). Of these, sodium carbonate is a preferred base. The coupling is generally performed in the presence of a suitable solvent or diluent, for example, a hydrocarbon (such as toluene or xylene), an ether (such as dioxan or tetrahydrofuran), an (1–4C)alcohol (such as methanol, ethanol or butanol), water or mixtures thereof (for example, a mixture of toluene, ethanol and water, which is preferred). The reaction is generally performed at a temperature in the range, for example, 50–150° C., and conveniently at or about the reflux temperature of the solvent or mixture of solvents used. Examples of step (c) are described in WO 96/40681, in Examples 1(iii), 11(ii), 12(ii), 13(ii), 14(ii), 58(vii) and 64(iv) thereof. Alternatively, the coupling may be carried out using a source of fluoride ion under aqueous conditions, for example using potassium fluoride in a mixture of toluene and water under reflux, by analogy with Example 30(ii) of WO 96/40681.

Removal of the isobutoxycarbonyl protecting group may be carried out after isolation of the protected product under basic conditions, such as by employing sodium hydroxide or alkoxide (e.g. methoxide) in a suitable solvent such as methanol (for example as described in Examples 1, 11, 12, 13, 14, 58 and 64 of WO 96/40681). Alternatively, the isobutoxycarbonyl group may be removed by in situ hydrolysis, for example, by addition of further water to the reaction mixture.

The process is particularly suitable for preparing the compound of formula I in which R is 2-carboxy-2-methylpropyl.

According to another aspect, the invention provides a process for the preparation of a compound of the formula I wherein R is 1,3,4-oxadiazol-2-yl which comprises steps (a) and (b) above followed by the additional steps of:

(i) reaction of 2-chloro-N-isobutoxycarbonyl-N-(3-methoxy-5-methylpyrazin-2-yl)pyridine-3-sulfonamide with 4-methoxycarbonylphenylboronic acid (or an anhydride or ester thereof) in the presence of a source of fluoride ion and under aqueous conditions to give N-(isobutoxycarbonyl)-2-(4-methoxycarbonylphenyl)-N-(3-methoxy-5-methylpyrazin-2-yl)pyridine-3-sulfonamide;

(ii) removal of the isobutoxycarbonyl protecting group;

(iii) conversion of the methyl ester (—CO.OCH$_3$) group to the corresponding hydrazide (—CONHNH$_2$); and (iv) conversion of the hydrazide group to a 1,3,4-oxadiazol-2-yl moiety; whereafter, when a pharmaceutically acceptable salt of a compound of formula I is required, it is obtained by reaction with the appropriate acid or base affording a physiologically-acceptable ion, or by any other conventional salt formation procedure.

Step (i) may be carried out, for example, by using potassium fluoride as the source of fluoride ion and employing as solvent a mixture of xylene, methanol and water, or a mixture of toluene and water. The reaction is conveniently carried out at the reflux temperature of the solvent mixture employed. A typical example of step (i) is exemplified in Example 30 (ii) of WO 96/40681.

Step (ii) may be carried out, for example, under basic conditions, such as by using a mixture of methanol and aqueous ammonia, or sodium methoxide in methanol. It may be carried out after first isolating the product obtained in (i) (as illustrated in Example 32 of WO 96/40681) or the reaction mixture from (i) may be diluted with water and the organic phase separated, filtered and the filtrate diluted with methanol, followed by the addition of aqueous ammonia. The product may then be isolated by addition of water and precipitation by addition of acetic acid.

Step (iii) may be carried out, for example, by reacting the product of step (ii) with hydrazine hydrate in a suitable solvent, such as dichloromethane and water. The hydrazide precipitates as the hydrazine salt and may be converted to the free hydrazide by addition of aqueous hydrochloric acid and isolated by filtration.

Step (iv) may be carried out, for example, by refluxing a mixture of the product of step (iii) in excess triethylorthoformate for 24 hours. The product precipitates on cooling. Alternatively steps (ii), (iii) and (iv) may be telescoped by reaction of the product of step (i) with hydrazine hydrate under reflux in a solvent such as methanol, ethanol, acetonitrile or tetrahydrofuran, followed by refluxing a mixture of the precipitated product is excess triethylorthoformate, as illustrated in Example 36 of WO 96/40681.

The invention will now be illustrated by the following non-limiting Examples in which, unless otherwise stated:

(i) yields are intended for the assistance of the reader only and are not necessarily the maximum attainable by diligent process development;

(ii) $^1$H NMR spectra were determined at 270 MH$_2$ in CDCl$_3$ using tetramethylsilane (TMS) as an internal standard, and are expressed as chemical shifts (delta values) in parts per million relative to TMS using conventional abbreviations for designation of major peaks: s, singlet; m, multiplet; t, triplet; br, broad; d, doublet.

EXAMPLE 1

Step 1

Thionyl chloride (42 ml) was added dropwise over 60 minutes to water (250 ml) cooled to 0° C., maintaining the temperature of the mixture between 0–7° C. The solution was allowed to warm to 18° C. over 17 hours. Copper (I) chloride (0.151 g) was added to the mixture and the resultant yellow-green solution was cooled to −3° C. using an ice/acetone bath.

Step 2

36% w/w hydrochloric acid (135 ml) was added, with agitation, to 3-amino-2-chloropyridine (17.3 g) maintaining the temperature of the mixture below 30° C. with ice cooling. The reaction mixture was cooled to −5° C. using an ice/acetone bath and a solution of sodium nitrite (10.0 g) in water (40 ml) was added dropwise over 45 minutes, maintaining the temperature of the reaction mixture between −5 and 0° C. The resultant slurry was cooled to −2° C. and stirred for 10 minutes.

Step 3

The slurry from Step 2 was cooled to −5° C. and added to the solution obtained from Step 1 over 95 minutes, maintaining the reaction temperature between −3° to 0° C. (The slurry from Step 2 was maintaining at −5° C. throughout the addition). As the addition proceeded, a solid began to precipitate. When the addition was complete, the reaction mixture was agitated at 0° C. for 75 minutes. The suspended solid was collected by vacuum filtration, washed with water (2×125 ml) and dried under vacuum at below 35° C. to give 2-chloropyridine-3-sulfonyl chloride (19.6 g; 70% yield); m.p. 42° C.; NMR: 7.50–7.60 (m, 1H), 8.45–8.50 (m, 1H) 8.72–8.75 (m, 1H).

Alternatively the product was isolated by extraction of the cold reaction mixture with toluene (100 ml), washing with water (2×100 ml) and drying the toluene extract by azeotropic distillation at reduced pressure (300 mm Hg). The dried toluene solution of the product was then used directly in a subsequent reaction.

EXAMPLE 2–10

Using an analogous procedure to that described in Example 1, the following sulfonyl chlorides were obtained starting from a proportionate amount of the appropriate aminopyridine or aminobenzene:

| Example | Product | Yield | Melting Point (° C.) | $^1$H NMR (δ, ppm) |
|---|---|---|---|---|
| 2 | 2-chloro-pyridine-5-sulfonyl chloride | 77 | 49–50 | 7.60 (d, 1H) 8.30 (dd, 1H) 9.03 (d, 1H) |
| 3 | pyridine-3-sulfonyl chloride | 38 | | 7.62 (bt, 1H) 8.20 (d, 1H) 8.21 (bs, 1H) |

-continued

| Example | Product | Yield | Melting Point (° C.) | ¹H NMR (δ, ppm) |
|---|---|---|---|---|
| 4 | 4-chlorobenzenesulfonyl chloride | 67 | 49–50 | 9.30 (bs, 1H)<br>7.60 (d, 2H)<br>7.99 (d, 2H) |
| 5 | 4-cyanobenzenesulfonyl chloride | 73 | 107–108 | 7.97 (d, 2H)<br>8.20 (d, 2H) |
| 6 | 3-nitrobeazenesulfonyl chloride | 80 | 41–45 | 7.90 (t, 1H)<br>8.37–8.40 (m, 1H)<br>8.60–8.62 (m, 1H)<br>8.89–8.91 (m, 1H) |
| 7 | 4- nitrobenzenesulfonyl chloride | 82 | 74–75 | 8.27 (d, 2H)<br>8.48 (d, 2H) |
| 8 | 4-(chlorosulfonyl)benzoic acid | 81 | 228–232 | 8.30 (d, 2H)<br>8.40 (d, 2H) |
| 9 | 2-bromobenzenesulfonyl chloride | 76 | 45–48 | 7.53–7.60 (m, 2H)<br>7.84–7.91 (m, 1H)<br>8.18-8.25 (m, 1H) |
| 10 | 3-chloro-4-cyanobenzenesulfonyl chloride | 78 | 51–54 | 7.98–8.10 (m, 2H)<br>8.20 (d, 1H) |

Notes:
(1) 3-pyridinesulfonyl chloride is an oil which was soluble in the reaction mixture and was isolated by extraction into dichloromethane.
(2) In Examples 4–10 the amine hydrochlorides precipitated as solids during the addition of the amine to the aqueous hydrochloric acid. To ensure complete salt formation the mixture was heated at 30 to 50° C. for up to 60 minutes prior to cooling and addition of the aqueous sodium nitrite solution.
(3) In Examples 4, 5 and 9, the products were obtained in two crops. The second crop precipitated from the combined aqueous mother liquor and wash filtrates.
(4) In Examples 4, 8 and 9, the products precipitated from their respective reaction mixtures after allowing them to warm to 20° C. and stirring at that temperature for 65, 17 and 27 hours respectively.
(5) In Example 6, the product initially precipitated from the reaction mixture as an oil which crystallised during the agitation period prior to filtration.
(6) In Example 8, the NMR spectrum was determined in d₃-acetonitrile
(7) In Examples 2–10 the copper(I) chloride was dissolved in the water prior to cooling and thionyl chloride addition

What I claim is:

1. A process for the manufacture of a compound of the formula I

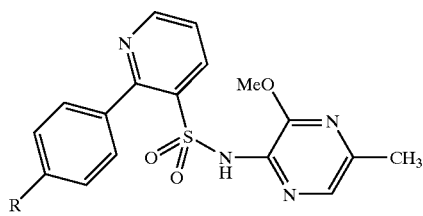

or a pharmaceutically acceptable salt thereof, wherein R is (1–4C)alkyl or carboxyl(1–4C)alkyl which comprises the steps of:

(a) reaction of the diazonium salt of 3-amino-2-chloropyridine with a mixture of thionyl chloride in water, in the presence of an electron transfer catalyst selected from cupric chloride and cuprous chloride, to give 2-chloropyridine-3-sulfonyl chloride;

(b) reaction of 2-chloropyridine-3-sulfonyl chloride with isobutyl N-(3-methoxy-5-methylpyrazin-2-yl) carbamate in the presence of an alkali metal hydride in an inert solvent to give 2-chloro-N-isobutoxycarbonyl-N-(3-methoxy-5-methylpyrazin-2-yl)pyridine-3-sulfonamide;

(c) reaction of 2-chloro-N-isobutoxycarbonyl-N-(3-methoxy-5-methylpyrazin-2-yl)pyridine-3-sulfonamide with a boronic acid at the formula II:

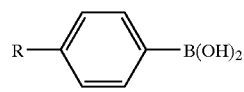

(or an anhydride or ester thereof) in the presence of a base and in the presence of a palladium (0), palladium (II), nickel (0) or nickel (II) catalyst in suitable solvent; followed by removal of the isobutoxy carbonyl protecting group;

whereafter when a pharmaceutically acceptable salt of a compound of formula I is required, it is obtained by reaction with the appropriate acid or base affording a physiologically-acceptable ion, or by any other conventional salt formation procedure.

2. A process for the manufacture of a compound of the formula I wherein R is 1,3,4-oxadiazol-2-yl which comprises (a) reaction of the diazonium salt of 3-amino-2-chloropyridine with a mixture of thionyl chloride in water, in the presence of an electron transfer catalyst selected from cupric chloride and cuprous chloride, to give 2-chloropyridine-3-sulfonyl chloride;

(b) reaction of 2-chloropyridine-3-sulfonyl chloride with isobutyl N-(3-methoxy-5-methylpyrazin-2-yl) carbamate in the presence of an alkali metal hydride in an inert solvent to give 2-chloro-N-isobutoxycarbonyl-N-(3-methoxy-5-methylpyrazin-2-yl)pyridine-3-sulfonamide (c) reaction of 2-chloro-N-isobutoxycarbonyl-N-(3-methoxy-5-methylpyrazin-2-yl)pyridine-sulfonamide with 4-methoxycarbonylphenylboronic acid (or an anhydride or ester thereof) in the presence of a source of fluoride ion and under aqueous conditions to give N-(isobutoxycarbonyl)-2-(4-methoxycarbonylphenyl)-N-(3-methoxy-5-methylpyrazin-2-yl)pyridine-3-sulfonamide;

(d) removal of the isobutoxycarbonyl protecting group;

(e) conversion of the methyl ester (—CO.OCH$_3$) group to the corresponding hydrazide (—CONHNH$_2$); and (f) conversion of the hydrazide group to a 1,3,4-oxadiazol-2-yl moiety; whereafter, when a pharmaceutically acceptable salt of a compound of formula I is required, it is obtained by reaction with the appropriate acid or base affording a physiologically-acceptable ion, or by any other conventional salt formulation procedure.

\* \* \* \* \*